US008634567B2

(12) United States Patent
Shim

(10) Patent No.: US 8,634,567 B2
(45) Date of Patent: Jan. 21, 2014

(54) METHOD OF AUTOMATICALLY FITTING HEARING AID

(76) Inventor: Yoon Joo Shim, Seoul (KR)

( * ) Notice: Subject to any disclaimer, the term of this patent is extended or adjusted under 35 U.S.C. 154(b) by 580 days.

(21) Appl. No.: 12/941,879

(22) Filed: Nov. 8, 2010

(65) Prior Publication Data

US 2011/0194706 A1 Aug. 11, 2011

(30) Foreign Application Priority Data

Feb. 10, 2010 (KR) ........................ 10-2010-0012507

(51) Int. Cl.
*H04R 29/00* (2006.01)
*A61B 5/00* (2006.01)

(52) U.S. Cl.
USPC ............................................ 381/60; 600/559

(58) Field of Classification Search
USPC .................. 381/60, 314, 312; 703/6; 600/559
See application file for complete search history.

(56) References Cited

U.S. PATENT DOCUMENTS 4,953,112 A * 8/1990 Widin et al. ...................... 703/6
5,386,475 A * 1/1995 Birck et al. ................... 381/320
7,068,793 B2 * 6/2006 Shim .............................. 381/60

FOREIGN PATENT DOCUMENTS

WO WO 9009760 A1 * 9/1990 ............... A61B 5/12
WO WO 9635314 A1 * 11/1996 ............ H04R 25/00

* cited by examiner

*Primary Examiner* — Mohammad Islam
*Assistant Examiner* — Phylesha Dabney
(74) *Attorney, Agent, or Firm* — Lee, Hong, Degerman, Kang & Waimey

(57) ABSTRACT

Provided is a method of automatically fitting a hearing aid. The method includes entering the audiogram of a test subject, defining criterion gains and SSPLs based on installed criterion gains and SSPLs according to the test subject's audiogram, generating sounds from automatic fitting device, measuring the sounds using probe microphone inserted in external earcanal, adjusting the criterion gain and SSPLs of the hearing aids based on differences between output sound amplitude and measured sound amplitude, and saving the changed values to the hearing aids automatically, in a state in which the hearing aid is worn by a test subject.

5 Claims, 4 Drawing Sheets

METHOD OF AUTOMATICALLY FITTING HEARING AID

CROSS-REFERENCE TO RELATED APPLICATIONS

Pursuant to 35 U.S.C. §119(a), this application claims the benefit of earlier filing date and right of priority to Korean Application No. 10-2010-0012507, filed on Feb. 10, 2010, the contents of which are hereby incorporated by reference herein in their entirety

FIELD OF THE DISCLOSURE

The present invention relates to a method of automatically fitting hearing aids, more specifically, to a method of adjusting a gain and a saturated sound pressure level (SSPL), i.e. a maximum output limit of amplification in a hearing aid when the hearing aid is worn in the ear of a user.

DISCUSSION OF THE RELATED ART

In general, the human ear is divided into three primary parts: an outer ear, a middle ear and an inner ear. The sound vibration occurring outside the ear is collected at pinna, directed to the tympanic membrane by earcanal of the outer ear.

The earcanal is a kind of a resonance tube, the end of which is closed by the eardrum. The vibration of the eardrum is directed to the inner ear through three small bones in the middle ear: namely, malleus, incus and stapes. When the vibration of the ossicles is transmitted to cochlea in the inner ear through the footplate of the stapes, endolymph inside the cochlea moves, and thousands of tiny hair cells in the scala media in the cochlea sense the vibration of the endolymph, the result of which is then converted to electrical signals. The electric signals are transmitted to the brain through the central nervous system, whereby sound perception occurs.

Meanwhile, hearing loss, which requires wearing of a hearing aid, may be classified into three types: conductive hearing loss, sensorineural hearing loss and mixed hearing loss. Hearing aids are also classified into three major types based on shape: pocket type, behind-the-ear type (BTE) and in-the-ear type (ITE). To use a hearing aid, the hearing aid should be fitted optimally and individually. Here, the phrase "hearing aid fitting" is used to mean a process of selecting an appropriate hearing aid according to the audiogram of hearing impaired person. periodically checking the hearing aid performances, the gain and SSPL of each frequency band are accurately tuned, thereby monitoring the hearing aid performance so as to be used without malfunction.

FIG. 1 is a flowchart illustrations a conventional method of the hearing aid fitting.

Referring to FIG. 1, patient's identification (ID) and audiogram are entered (steps S1 to S2), a couple of hearing aid conditions, i.e. the type of hearing aid and the shape of ear structure are set (S3), and then 'Best fit' is selected (S4). When best fit is selected, criterion values for gain and SSPL obtained by the 2 cc coupler gain and insertion gain is set regardless of individual state and condition. Here, the insertion gain is an average difference between unaided and aided gain, and the 2 cc coupler gain is a mechanical average gain standardized to normal earcanal volume of a Caucasian adults with no wearing earmold connected to the hearing aids.

The patient then wears hearing aids and signals of the amplitudes of 50 dB SPL are swept outputted for each frequency range, and the wearer is required to report whether stimuli of each frequency band are equally loud. According to the response of the patient, the setting, i.e. gain and SSPL of the hearing aid (s5 to S7) is changed.

As above, the conventional hearing aid fitting method requires a quite long time, and it adopts gain and SSPL average criterion values based on insertion gain or 2 cc coupler gain, irrespective of individual state such as size of external earcanal, shape of earmold, location of the microphone of hearing aid and the like, thus it is impossible to achieve accurate individual fitting so as to be tailored to an individual user.

Also, hearing loss can be worsened by overamplification, and several revisits for readjustment are a cumbersome routine procedure.

Moreover, since the user's subjective cooperation is required in fitting procedure, conventional procedures are a method inappropriate for infants or elderly persons.

SUMMARY OF THE DISCLOSURE

It is an object of the present invention is to provide a method of automatically fitting hearing aids, by generating sounds from automatic fitting device, measuring the sounds using a probe microphone inserted in external earcanal, adjusting the criterion gain and SSPLs of the hearing aids based on differences between output sound amplitude and measured sound amplitude, and entering the changed values to the hearing aids automatically, in a state in which the hearing aid is worn by a test subject.

It is another object of the invention to prevent the hearing loss caused by overamplification, from worsening by providing a method of automatically fitting hearing aids, which has suitable SSPLs and ideal word recognition.

In an embodiment, the above objects are accomplished by a method of automatically fitting hearing aids, by inserting the probe microphone in the ear of the test subject in a state in which the hearing aid is worn by a test subject, and measuring the output sound from the automatic fitting device using probe microphone; when audiogram of the test subject is entered to the automatic fitting device, the device calculates the criterion gain and SSPLs based on installed criterion gains and SSPLs, the probe microphone measures the sounds generated for each frequency band, calculates the differences between the output amplitudes and the measure amplitudes, then adjusts the criterion gain and SSPLs and enters the values to the hearing aids.

Here, the step of adjusting the criterion gains and SSPLs may include adding or reducing the calculated differences from the criterion gain and SSPLs.

Also, the step of calculating the differenced for each frequency bandwidth and adjusting the criterion gain and SSPLs according to the calculated differences may include computing the differences by reducing the amplitude of the output sound from the amplitude of the measured sound, and then reducing the calculated differences from the criterion gains and SSPLs.

Meanwhile, the output sound is a long term speech spectrum noise of 70 dB sound pressure level.

And, the criteria gain is a standardized value from a first sound measured by the probe microphone, SSPL is standardized value from a second sound measured by the probe microphone. Here, the first sound is a long term speech spectrum noise of 70 dB sound pressure level, and the second sound is the signal tone of 90 dB sound pressure level.

As above, the method of automatically fitting hearing aids by the embodiment of the invention may produces the following effects;

First, the criteria gain and SSPL of the hearing aid can be adjusted automatically and accurately, by setting the automatic fitting device using precise rear ear criteria value chosen from test subject's audiogram, and by adjusting the criteria gain and SSPL of the hearing aid from the error of standardized criteria value calculated from the difference between real sensed sound and output sound by speaker if the automatic fitting device.

Second, the criteria gain and SSPL of the hearing aid can be adjusted rapidly and suitably for individual state, which makes readjustment unnecessary.

Third, Fitting method can be applied to infants or elderly persons since user's subjective cooperation is unnecessary in fitting procedure. Particularly, the method can be applied to the infants and the patient in an unconscious state by measure the audiogram of the patient using brainstem response electric audiometry, thus it enables the early hearing-rehabilitation such as preventing delayed speech.

Fourth, only one type of model is required for manufacturing, to contribute to financial gain.

Fifth, against the conventional method, the method needs no help from an expert, to greatly reduce maintenance cost.

BRIEF DESCRIPTION OF THE DRAWINGS

Further objects and advantages of the invention can be more fully understood from the following detailed description taken in conjunction with the accompanying drawings in which.

DETAILED DESCRIPTION OF PREFERRED EMBODIMENTS

Figure 1:
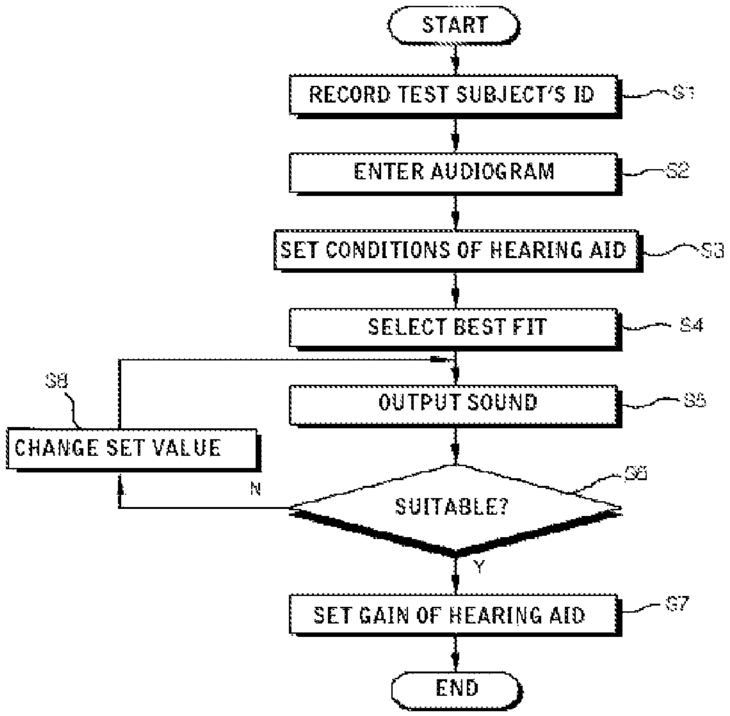
FIG. 1 is a flow chart showing a conventional method of fitting a hearing aid.
Figure 2:
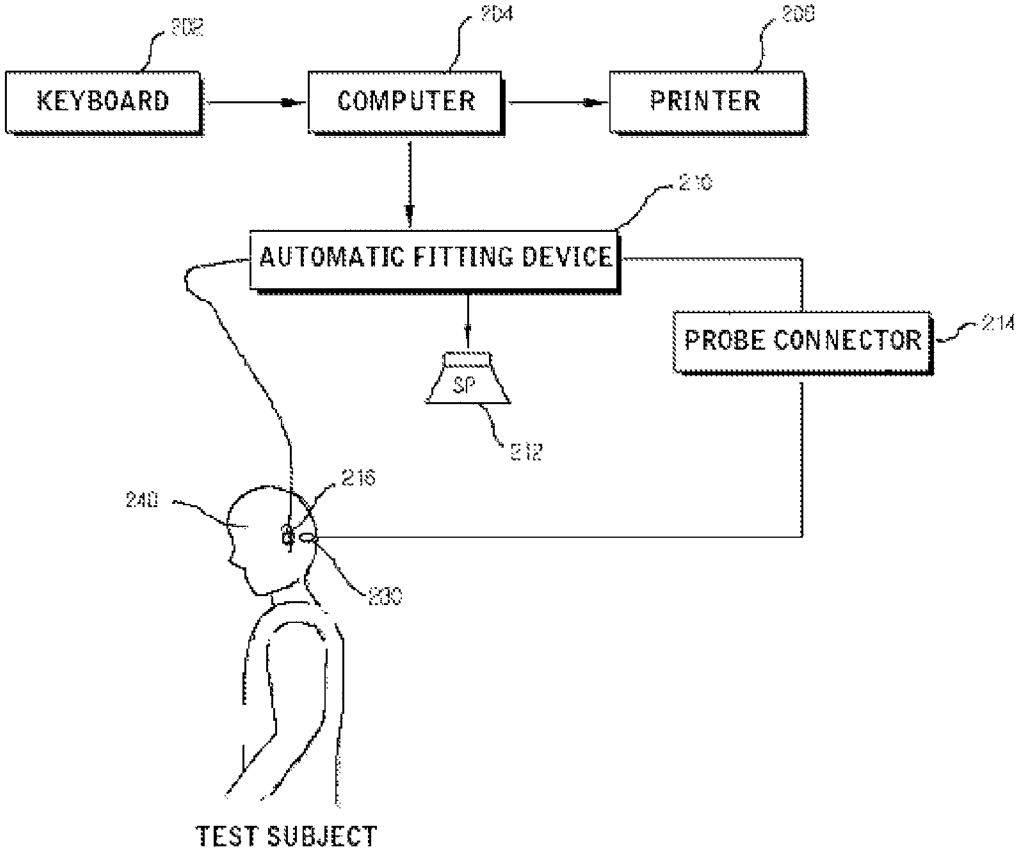
FIG. 2 shows in summarized form the automatically fitting system according to the invention.

FIG. 2 shows in summarized form the automatically fitting system according to an embodiment of the invention.

Referring to FIG. 2, the automatically fitting system includes a keyboard 202, a computer 204, a printer 206, an automatic fitting device 210, a speaker 212, a probe connector 214 connected to a hearing aid 230, a probe microphone 216 connected to the automatic fitting device 210, and the hearing aid 230 connected to the probe connector 214.

The computer 204 has an operating system (O/S) and fitting-related program loaded therein. In response to an operator's manipulation of the keyboard 202, the computer 204 controls the automatic fitting device 210 and manages various kinds of data. Also, the computer 204 monitors the operation state to exhibit the monitored data to the operator and allows the result to be printed by the printer 206.

The automatic fitting device 210 is a means performing the whole fitting process controlled by the computer 204, monitors the conversation sound transmitted to the eardrum, which is the results of all the parameters taken into account. The automatic fitting device 210 is designed to calculate the difference between the measured amplitude of the conversation sound and the input amplitude of the conversation sound, to adjust the criteria gain and SSPL of the patient for each frequency region (such as 250, 500, 750, 1000, 1500, 2000, 3000, 4000 and 6000 Hz), to enter the changed criteria gain and SSPL to the hearing aid 230 through the probe connector 214.

Here, adjusting the criterion gain and SSPLs according to the calculated differences from the automatic fitting device 210 is computing the differences by reducing the amplitude of the output sound from the amplitude of the measured sound, and then reducing the calculated differences from the criterion gains and SSPLs.

The automatic fitting device 210 preferably employs a PFS 6000 model, but can be applied to any kinds of digital hearing aid fitting systems.

Figure 3:
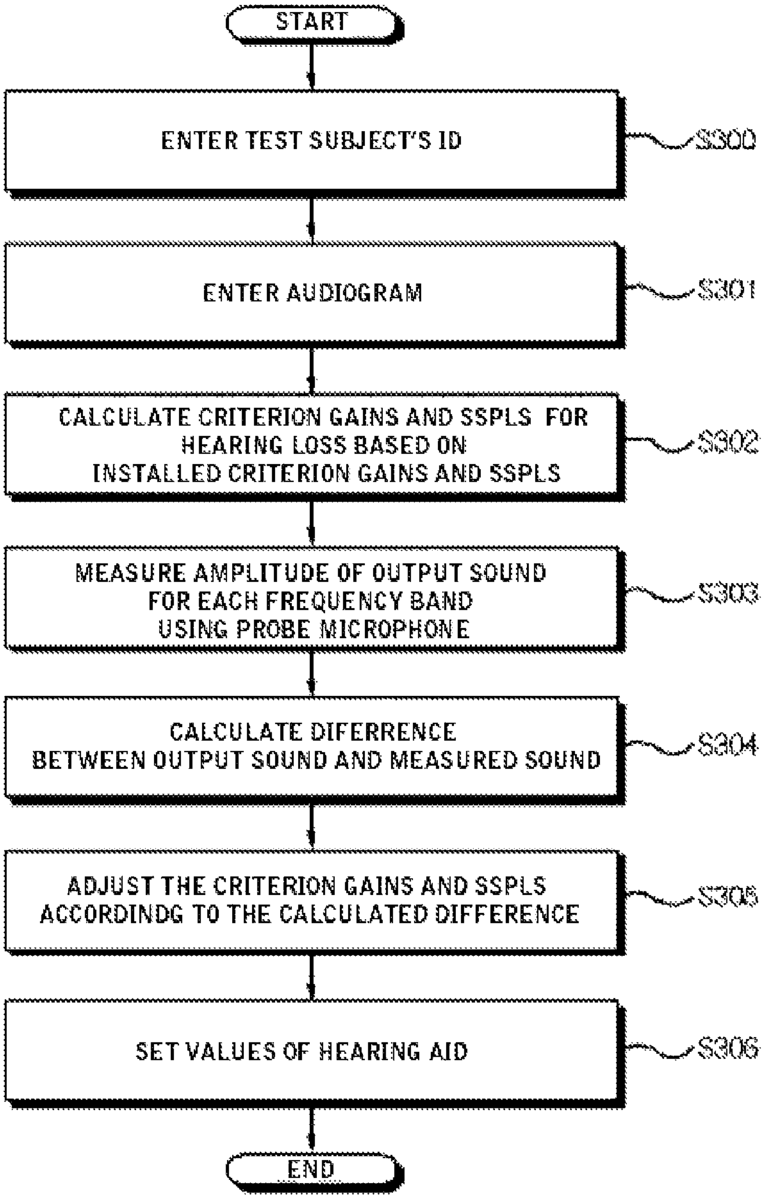
FIG. 3 is a flow chart showing a method of automatically fitting a hearing aid according to the invention.

FIG. 3 is a flow chart showing a method of automatically fitting a hearing aid according to an embodiment of the invention;

Referring to FIG. 3, first, the fitting criteria gain and the SSPL are installed to the automatic fitting device 210 for every 5 dB increase of the frequency range. Here, the criteria gain and SSPL is standardized for hearing loss at each frequency band, and the criteria gain is the suitable level value for each frequency region such as 250, 500, 750, 1000, 1500, 2000, 3000, 4000 and 6000 Hz, standardized from the 70 dB SPL long term speech spectrum noise output by speaker 212 measured by the probe microphone 216 in rear ear, that is, in the state in which the hearing aid 230 is worn by test subjects, more than 5 hundreds patients, and the probe microphone 216 is inserted in the external earcanal in front of the eardrum which is 60 cm far from the hearing aid 230.

Also, the SSPL is the suitable level value standardized from the sound measured by the probe microphone 216 using the signal tone of 90 dB sound pressure level instead of the 70 dB sound pressure level.

Figure 4:
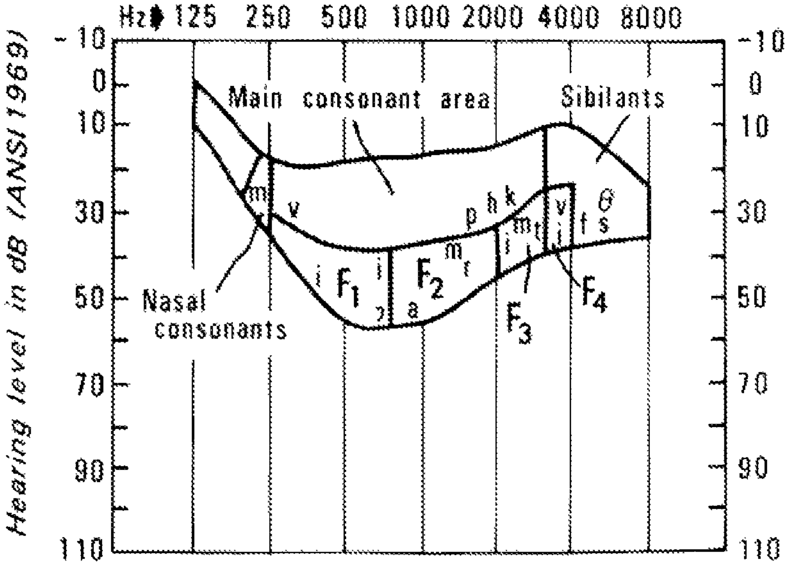
FIG. 4 is a diagram representing long term average spectrum, i.e. the average amplitude of the conversation sound versus the frequency.

FIG. 4 is a diagram representing long term average spectrum, i.e. the average amplitude of the conversation sound versus the frequency. Nasal sound and sibilance sound region is represented as hearing level for each frequency region.

To perform the method of automatically fitting system, in steps S300 and S301, enter the patient's identification and the audiogram to monitor the each patient's data.

To measure the patient's audiogram, the pure tone measurement is required, using the pure tone audiometer. The pure tone audiometer provides the pure tone signal of 250, 500, 750, 1000, 1500, 2000, 3000, 4000, 6000 and 8000 Hz to the patient, while put the earphone of the audiometer at subject's ear and regulating the dial. Again, measure the hearing threshold level from reduce the dial tone.

Next, in step S302, decide the criteria gain and SSPL for the subject's audiogram from installed criterion gains and SSPLs already.

And then, in step S303, measure the sound for each frequency range using the probe microphone 216. More particularly, in a state in which the hearing aid is worn by a test subject while probe microphone 216 is inserted in the external earcanal, measure the long term speech spectrum noise of 70 dB sound pressure level generated from the speaker 212 of the automatic fitting device 210 using the probe microphone 216.

Then, in step S304, compare and calculate the difference between the amplitude of the output sound from the speaker 212 of the automatic fitting device 210 and the amplitude of the sound measured for each frequency region.

Then, in step S305, adjust the criteria gain and SSPL according to the difference from the step s304. More particularly, for the patient having threshold for 250 Hz is 50 dB and for 500 Hz is 60 dB, his criteria gain and SSPL for each frequency region is already installed and set; At 250 Hz for 50 dB hearing loss the criteria gain is 19 and SSPL is 90, and at 500 Hz for 50 dB hearing loss the criteria gain is 21 and SSPL is 93; The difference between the amplitude of the output sound from the speaker 212 and the amplitude of the sound measured at the probe microphone 216 is −5 dB for 250 Hz and 3 dB for 500 Hz; Again, at 250 Hz, the amplitude of the sound measured at the probe microphone 216 is 5 dB less than the amplitude of the output sound from the speaker 212, i.e. the subject hears the sound smaller than the real output sound; Thus the criteria gain should be adjusted 5 dB more than the preset, as a result, 19+5=24 dB; Samely, SSPLs should be adjusted for 90+5=95 dB;

Also, at 500 Hz, the amplitude of the sound measured at the probe microphone 216 is 3 dB more than the amplitude of the output sound from the speaker 212, i.e. the subject hears the sound louder than the real output sound; Thus the criteria gain should be adjusted 5 dB more than the preset, as a result, 21−3=18 dB; Samely, SSPLs should be adjusted for 93−3=90 dB;

Entering the changed criteria gain and SSPL to the hearing aid 306, the method of automatically fitting individual hearing aids is complete in step S306.

What is claimed is:

1. A method of automatically fitting a hearing aid, the method performed by an automatic fitting device including a probe microphone, the method comprising:

obtaining an audiogram of a test subject;

determining an initial gain for the hearing aid at each frequency band of a plurality of frequency bands, each initial gain based on the audiogram and standardized gain values;

determining an initial saturated sound pressure level (SSPL) for the hearing aid at each frequency band of the plurality of frequency bands, each initial SSPL based on the audiogram and standardized SSPL values;

setting the hearing aid with the initial gains and the initial SSPLs;

generating an external sound while the hearing aid set with the initial gains and the initial SSPLs is worn by the test subject and the probe microphone is positioned in the ear canal of the test subject;

measuring amplitude information of sound output by the hearing aid for each frequency band of the plurality of frequency bands with the probe microphone while the external sound is generated;

comparing, for each frequency band of the plurality of frequency bands, the amplitude information of the sound output by the hearing aid with amplitude information of the external sound;

determining, for each frequency band of the plurality of frequency bands, a corrected gain and a corrected SSPL based on a result of the comparison for the corresponding frequency band; and setting the hearing aid with the corrected gains and the corrected SSPLs.

2. The method according to claim 1, wherein:

comparing the amplitude information of the sound output by the hearing aid with the amplitude information of the external sound includes determining a difference in amplitude; and determining the corrected gain and the corrected SSPL includes adding the difference in amplitude to the initial gain and the initial SSPL or subtracting the difference in amplitude from the initial gain and the initial SSPL.

3. The method according to claim 1, wherein the generated external sound is a long term speech spectrum noise of 70 dB sound pressure level.

4. The method according to claim 1, wherein:

the generated external sound includes a first external sound and a second external sound;

measuring the amplitude information of sound output by the hearing aid includes measuring a first amplitude of a first sound output by the hearing aid while the first external sound is generated and measuring a second amplitude of a second sound output by the hearing aid while the second external sound is generated;

comparing the amplitude information includes comparing the first amplitude with an amplitude of the first external sound to obtain a first result and comparing the second amplitude with an amplitude of the second external sound to obtain a second result; and the corrected gain for each corresponding frequency band is determined based on the first result, and the corrected SSPL for each corresponding frequency band is determined based on the second result.

5. The method according to claim 4, wherein the first external sound is a long term speech spectrum noise of 70 dB sound pressure level, and the second external sound is white noise of 90 dB sound pressure level.

* * * * *